(12) United States Patent
Stewart et al.

(10) Patent No.: US 7,927,313 B2
(45) Date of Patent: Apr. 19, 2011

(54) MEDICAL DEVICE CONFIGURATION BASED ON RECOGNITION OF IDENTIFICATION INFORMATION

(75) Inventors: Janice Stewart, Inverness, IL (US); Randolph Meinzer, Spring Grove, IL (US); Debra K. Bello, Vernon Hills, IL (US); Janet Mullan, Antioch, IL (US); Alan Brundle, Barrington, IL (US); James D. Jacobson, Lindenhurst, IL (US); Tuan Bui, Green Oaks, IL (US); Qui Chau, Skokie, IL (US)

(73) Assignee: Baxter International Inc., Deerfield, IL (US)

( * ) Notice: Subject to any disclaimer, the term of this patent is extended or adjusted under 35 U.S.C. 154(b) by 1130 days.

(21) Appl. No.: 10/855,855

(22) Filed: May 27, 2004

(65) Prior Publication Data
US 2005/0277890 A1    Dec. 15, 2005

(51) Int. Cl.
*A61M 3/00* (2006.01)
*A61M 5/00* (2006.01)
*H04Q 11/00* (2006.01)
*H04L 12/16* (2006.01)
*G06F 17/00* (2006.01)

(52) U.S. Cl. ........................................ 604/189; 235/375
(58) Field of Classification Search ............ 604/48, 604/93.01, 189; 235/375
See application file for complete search history.

(56) References Cited

U.S. PATENT DOCUMENTS

| | | | |
|---|---|---|---|
| 3,391,694 A * | 7/1968 | Spaeth | 604/189 |
| 3,715,058 A | 2/1973 | Clymans | |
| 3,809,871 A * | 5/1974 | Howard et al. | 604/500 |
| 3,877,428 A | 4/1975 | Seagle et al. | |
| 3,925,762 A | 12/1975 | Heitlinger et al. | |
| 4,028,539 A | 6/1977 | Jacobs | |
| 4,180,067 A | 12/1979 | Derlien | |
| 4,216,462 A | 8/1980 | McGrath et al. | |
| 4,282,872 A * | 8/1981 | Franetzki et al. | 604/67 |

(Continued)

FOREIGN PATENT DOCUMENTS

JP      3-140164      6/1991

(Continued)

OTHER PUBLICATIONS

Final Rejection from USPTO for U.S. Appl. No. 10/855,872, May 14, 2009.

(Continued)

*Primary Examiner* — Nicholas D Lucchesi
*Assistant Examiner* — Michael J Anderson
(74) *Attorney, Agent, or Firm* — K&L Gates LLP

(57) ABSTRACT

A medical delivery system (10) is provided for delivering a medicament (17) or fluid (17) to a patient. The system comprises a disposable element such as a line set (14) associated with a container (16) containing the fluid (17), an identifier (18) associated with the line set (14) and having identification information associated therewith, and a delivery device (12) configured to engage the line set (14) and deliver the fluid (17) to the patient. The delivery device (12) includes a recognition system (20) that is capable of obtaining the identification information associated with the identifier (18). The identification information may include information regarding the identification of the fluid (17), a type of line set (14), or a type of administration associated with the line set (14). The device (12) can be capable of configuration based on the identification information.

27 Claims, 4 Drawing Sheets

U.S. PATENT DOCUMENTS

| | | | |
|---|---|---|---|
| 4,391,598 A | 7/1983 | Thompson | |
| 4,431,425 A | 2/1984 | Thompson et al. | |
| 4,464,172 A | 8/1984 | Lichtenstein | |
| 4,493,704 A | 1/1985 | Beard et al. | |
| 4,493,709 A | 1/1985 | Smith | |
| 4,498,843 A | 2/1985 | Schneider et al. | |
| 4,529,401 A | 7/1985 | Leslie et al. | |
| 4,553,958 A | 11/1985 | LeCocq et al. | |
| 4,616,801 A | 10/1986 | Cewers et al. | |
| 4,624,661 A * | 11/1986 | Arimond | 604/151 |
| 4,657,490 A | 4/1987 | Abbott | |
| 4,658,375 A | 4/1987 | Onogi et al. | |
| 4,678,458 A * | 7/1987 | Fredeking | 604/6.04 |
| 4,696,671 A | 9/1987 | Epstein et al. | |
| 4,710,166 A * | 12/1987 | Thompson et al. | 604/81 |
| 4,714,462 A | 12/1987 | DiDomenico | |
| 4,715,385 A | 12/1987 | Cudahy et al. | |
| 4,741,736 A | 5/1988 | Brown | |
| 4,776,842 A | 10/1988 | Franetzki et al. | |
| 4,785,799 A | 11/1988 | Schoon et al. | |
| 4,810,243 A | 3/1989 | Howson | |
| 4,820,273 A | 4/1989 | Reinicke | |
| 4,828,545 A | 5/1989 | Epstein et al. | |
| 4,838,887 A | 6/1989 | Idriss | |
| 4,840,542 A | 6/1989 | Abbott | |
| 4,842,584 A | 6/1989 | Pastrone | |
| 4,857,048 A * | 8/1989 | Simons et al. | 604/503 |
| 4,857,713 A | 8/1989 | Brown | |
| 4,865,584 A | 9/1989 | Epstein et al. | |
| 4,867,170 A | 9/1989 | Takahashi | |
| 4,878,175 A | 10/1989 | Norden-Paul et al. | |
| 4,895,161 A | 1/1990 | Cudahy et al. | |
| 4,931,050 A | 6/1990 | Idriss | |
| 4,943,279 A | 7/1990 | Samiotes et al. | |
| 4,978,335 A | 12/1990 | Arthur, III | |
| 5,002,055 A | 3/1991 | Merki et al. | |
| 5,034,004 A | 7/1991 | Crankshaw | |
| 5,049,141 A | 9/1991 | Olive | |
| 5,072,383 A | 12/1991 | Brimm et al. | |
| 5,077,666 A | 12/1991 | Brimm et al. | |
| 5,078,683 A * | 1/1992 | Sancoff et al. | 604/67 |
| 5,100,380 A * | 3/1992 | Epstein et al. | 604/67 |
| 5,108,367 A | 4/1992 | Epstein et al. | |
| 5,108,372 A | 4/1992 | Swenson | |
| 5,205,819 A | 4/1993 | Ross et al. | |
| 5,207,666 A | 5/1993 | Idriss et al. | |
| 5,219,330 A | 6/1993 | Bollish et al. | |
| 5,274,551 A | 12/1993 | Corby, Jr. | |
| 5,290,239 A | 3/1994 | Classey et al. | |
| 5,300,044 A | 4/1994 | Classey et al. | |
| 5,304,126 A | 4/1994 | Epstein et al. | |
| 5,314,243 A | 5/1994 | McDonald et al. | |
| 5,317,506 A | 5/1994 | Coutre et al. | |
| 5,325,478 A | 6/1994 | Shelton et al. | |
| 5,368,562 A | 11/1994 | Blomquist et al. | |
| 5,378,231 A | 1/1995 | Johnson et al. | |
| 5,379,333 A | 1/1995 | Toth | |
| 5,395,340 A | 3/1995 | Lee | |
| 5,400,378 A | 3/1995 | Toth | |
| 5,429,602 A | 7/1995 | Hauser | |
| 5,445,621 A | 8/1995 | Poli et al. | |
| 5,458,123 A | 10/1995 | Unger | |
| 5,460,490 A | 10/1995 | Carr et al. | |
| 5,464,392 A | 11/1995 | Epstein et al. | |
| 5,483,957 A | 1/1996 | Janssen et al. | |
| 5,507,412 A | 4/1996 | Ebert et al. | |
| 5,514,088 A | 5/1996 | Zakko | |
| 5,522,798 A | 6/1996 | Johnson et al. | |
| 5,547,470 A | 8/1996 | Johnson et al. | |
| 5,558,638 A | 9/1996 | Evers et al. | |
| 5,558,640 A | 9/1996 | Pfeiler et al. | |
| 5,564,803 A | 10/1996 | McDonald et al. | |
| 5,573,506 A | 11/1996 | Vasko | |
| 5,586,868 A | 12/1996 | Lawless et al. | |
| 5,591,344 A | 1/1997 | Kenley et al. | |
| 5,628,619 A | 5/1997 | Wilson | |
| 5,640,953 A | 6/1997 | Bishop et al. | |
| 5,643,212 A | 7/1997 | Coutre et al. | |
| 5,647,854 A | 7/1997 | Olsen et al. | |
| 5,658,250 A | 8/1997 | Blomquist et al. | |
| 5,681,285 A | 10/1997 | Ford et al. | |
| 5,685,844 A | 11/1997 | Marttila | |
| 5,713,856 A | 2/1998 | Eggers et al. | |
| 5,718,562 A | 2/1998 | Lawless et al. | |
| 5,739,508 A | 4/1998 | Uber, III | |
| 5,745,378 A | 4/1998 | Barker et al. | |
| 5,752,917 A | 5/1998 | Fuchs | |
| 5,772,635 A | 6/1998 | Dastur et al. | |
| 5,778,882 A | 7/1998 | Raymond et al. | |
| 5,781,442 A | 7/1998 | Engleson et al. | |
| 5,782,805 A * | 7/1998 | Meinzer et al. | 604/131 |
| 5,791,880 A | 8/1998 | Wilson | |
| 5,795,327 A * | 8/1998 | Wilson et al. | 604/65 |
| 5,807,321 A | 9/1998 | Stoker et al. | |
| 5,810,770 A | 9/1998 | Chin et al. | |
| 5,814,015 A | 9/1998 | Gargano et al. | |
| 5,816,242 A | 10/1998 | Cewers | |
| 5,830,187 A | 11/1998 | Kriesel et al. | |
| 5,836,910 A | 11/1998 | Duffy et al. | |
| 5,852,590 A | 12/1998 | De La Huerga | |
| 5,871,465 A | 2/1999 | Vasko | |
| 5,883,576 A | 3/1999 | De La Huerga | |
| 5,897,498 A | 4/1999 | Canfield, II et al. | |
| D410,081 S | 5/1999 | Sweeney et al. | |
| 5,903,889 A | 5/1999 | De La Huerga et al. | |
| 5,925,014 A * | 7/1999 | Teeple Jr. | 358/1.15 |
| 5,935,099 A | 8/1999 | Peterson et al. | |
| 5,938,607 A | 8/1999 | Jago et al. | |
| 5,941,846 A | 8/1999 | Duffy et al. | |
| 5,957,885 A | 9/1999 | Bollish et al. | |
| 5,960,085 A | 9/1999 | De La Huerga | |
| 5,980,501 A * | 11/1999 | Gray | 604/408 |
| 6,012,034 A | 1/2000 | Hamparian et al. | |
| 6,032,155 A | 2/2000 | De La Huerga | |
| 6,044,134 A | 3/2000 | De La Huerga | |
| 6,045,533 A | 4/2000 | Kriesel et al. | |
| 6,077,055 A | 6/2000 | Vilks | |
| 6,081,048 A | 6/2000 | Bergmann et al. | |
| 6,095,985 A | 8/2000 | Raymond et al. | |
| 6,104,941 A | 8/2000 | Huey et al. | |
| 6,108,399 A | 8/2000 | Hernandez-Guerra et al. | |
| RE36,871 E * | 9/2000 | Epstein et al. | 604/67 |
| 6,117,126 A | 9/2000 | Appelbaum et al. | |
| 6,123,686 A | 9/2000 | Olsen et al. | |
| 6,129,702 A | 10/2000 | Woias et al. | |
| 6,139,495 A | 10/2000 | De La Huerga | |
| 6,141,402 A | 10/2000 | Toth | |
| 6,167,012 A | 12/2000 | Van Den Enden et al. | |
| 6,182,076 B1 | 1/2001 | Yu et al. | |
| 6,183,417 B1 | 2/2001 | Geheb et al. | |
| 6,216,104 B1 | 4/2001 | Moshfeghi et al. | |
| 6,231,560 B1 | 5/2001 | Bui et al. | |
| 6,241,704 B1 | 6/2001 | Peterson et al. | |
| 6,255,951 B1 | 7/2001 | De La Huerga | |
| 6,257,936 B1 | 7/2001 | Strandberg | |
| 6,259,654 B1 | 7/2001 | De La Huerga | |
| 6,260,021 B1 | 7/2001 | Wong et al. | |
| 6,264,614 B1 | 7/2001 | Albert et al. | |
| 6,269,340 B1 | 7/2001 | Ford et al. | |
| 6,272,505 B1 | 8/2001 | De La Huerga | |
| 6,283,944 B1 | 9/2001 | McMullen et al. | |
| 6,285,285 B1 * | 9/2001 | Mongrenier | 340/572.8 |
| 6,308,171 B1 | 10/2001 | De La Huerga | |
| 6,312,227 B1 | 11/2001 | Davis | |
| 6,345,268 B1 | 2/2002 | De La Huerga | |
| 6,346,886 B1 | 2/2002 | De La Huerga | |
| 6,350,239 B1 | 2/2002 | Ohad et al. | |
| 6,356,780 B1 | 3/2002 | Licato et al. | |
| 6,358,237 B1 | 3/2002 | Paukovits et al. | |
| 6,377,223 B1 | 4/2002 | Clapp et al. | |
| 6,401,138 B1 | 6/2002 | Judge et al. | |
| 6,405,165 B1 | 6/2002 | Blum et al. | |
| 6,408,330 B1 | 6/2002 | De La Huerga | |
| 6,409,659 B1 | 6/2002 | Warner et al. | |
| 6,409,696 B1 | 6/2002 | Toavs et al. | |
| 6,416,495 B1 | 7/2002 | Kriesel et al. | |
| 6,434,567 B1 | 8/2002 | De La Huerga | |

| | | |
|---|---|---|
| 6,450,956 B1 | 9/2002 | Rappaport et al. |
| 6,462,953 B2 | 10/2002 | Tong et al. |
| 6,468,242 B1 | 10/2002 | Wilson et al. |
| 6,471,645 B1 | 10/2002 | Warkentin et al. |
| 6,471,675 B1 | 10/2002 | Rogers et al. |
| 6,648,242 B2 | 10/2002 | Wilson et al. |
| 6,475,146 B1 | 11/2002 | Frelburger et al. |
| 6,475,148 B1 | 11/2002 | Jackson et al. |
| 6,475,178 B1 | 11/2002 | Krajewski et al. |
| 6,475,180 B2 | 11/2002 | Peterson et al. |
| 6,497,656 B1 | 12/2002 | Evans et al. |
| 6,497,680 B1 | 12/2002 | Holst et al. |
| 6,504,837 B1 | 1/2003 | Menzel |
| 6,506,155 B2 | 1/2003 | Sluis |
| 6,519,569 B1 | 2/2003 | White et al. |
| 6,520,910 B1 | 2/2003 | Kohls |
| 6,529,654 B1 | 3/2003 | Wong et al. |
| 6,537,214 B1 | 3/2003 | Hood et al. |
| 6,537,244 B2 | 3/2003 | Paukovits et al. |
| 6,539,504 B1 | 3/2003 | Knefel |
| 6,542,902 B2 | 4/2003 | Dulong et al. |
| 6,547,748 B1 | 4/2003 | Shine |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,562,001 B2 | 5/2003 | Lebel et al. |
| 6,571,128 B2 | 5/2003 | Lebel et al. |
| 6,611,733 B1 | 8/2003 | De La Huerga |
| 6,626,862 B1 * | 9/2003 | Duchon et al. ............... 604/110 |
| 6,671,563 B1 | 12/2003 | Engelson et al. |
| 6,731,989 B2 | 5/2004 | Engleson et al. |
| 6,779,024 B2 | 8/2004 | De La Huerga |
| 6,790,198 B1 | 9/2004 | White et al. |
| 6,840,482 B2 | 1/2005 | Boyne-Aitken |
| 6,840,492 B1 * | 1/2005 | Boyne-Aitken ............... 251/7 |
| 6,915,170 B2 | 7/2005 | Engleson et al. |
| 6,985,870 B2 * | 1/2006 | Martucci et al. ............... 705/3 |
| 7,006,894 B2 | 2/2006 | De La Huerga |
| 7,061,831 B2 | 6/2006 | De La Huerga |
| 7,074,205 B1 | 7/2006 | Duffy et al. |
| 7,077,328 B2 | 7/2006 | Krishnaswamy et al. |
| 7,096,072 B2 | 8/2006 | Engleson et al. |
| 7,103,419 B2 | 9/2006 | Engleson et al. |
| 7,107,106 B2 | 9/2006 | Engleson et al. |
| 7,115,113 B2 * | 10/2006 | Evans et al. ............... 604/189 |
| 7,117,041 B2 | 10/2006 | Engleson et al. |
| 7,171,277 B2 | 1/2007 | Engleson et al. |
| 7,216,802 B1 | 5/2007 | De La Huerga |
| 7,236,936 B2 | 6/2007 | White et al. |
| 7,384,410 B2 | 6/2008 | Eggers et al. |
| 7,398,183 B2 | 7/2008 | Holland et al. |
| 7,454,314 B2 | 11/2008 | Holland et al. |
| 7,483,756 B2 | 1/2009 | Engleson et al. |
| 7,490,021 B2 | 2/2009 | Holland et al. |
| 2001/0017817 A1 | 8/2001 | De La Huerga |
| 2001/0020148 A1 | 9/2001 | Sasse et al. |
| 2001/0025156 A1 | 9/2001 | Bui et al. |
| 2001/0028308 A1 | 10/2001 | De La Huerga |
| 2001/0031944 A1 | 10/2001 | Peterson et al. |
| 2001/0037083 A1 | 11/2001 | Hartlaub et al. |
| 2001/0040127 A1 * | 11/2001 | Donig et al. ............... 210/321.71 |
| 2001/0044731 A1 | 11/2001 | Coffman et al. |
| 2002/0002326 A1 | 1/2002 | Causey, III et al. |
| 2002/0016568 A1 | 2/2002 | Lebel et al. |
| 2002/0019606 A1 | 2/2002 | Lebel et al. |
| 2002/0029776 A1 | 3/2002 | Blomquist |
| 2002/0038392 A1 * | 3/2002 | De La Huerga ............... 710/8 |
| 2002/0058906 A1 | 5/2002 | Lebel et al. |
| 2002/0061255 A1 | 5/2002 | Nguyen et al. |
| 2002/0065454 A1 | 5/2002 | Lebel et al. |
| 2002/0065509 A1 | 5/2002 | Lebel et al. |
| 2002/0065540 A1 | 5/2002 | Lebel et al. |
| 2002/0072733 A1 | 6/2002 | Flaherty |
| 2002/0077852 A1 | 6/2002 | Ford et al. |
| 2002/0077865 A1 | 6/2002 | Sullivan |
| 2002/0087120 A1 | 7/2002 | Rogers et al. |
| 2002/0107476 A1 | 8/2002 | Mann et al. |
| 2002/0116509 A1 | 8/2002 | De La Huerga |
| 2002/0123740 A1 | 9/2002 | Flaherty et al. |
| 2002/0126035 A1 | 9/2002 | Hou |
| 2002/0151875 A1 | 10/2002 | Haller |
| 2002/0156462 A1 | 10/2002 | Stultz |
| 2002/0177821 A1 | 11/2002 | Barak |
| 2002/0188259 A1 | 12/2002 | Hickle et al. |
| 2002/0198513 A1 | 12/2002 | Lebel et al. |
| 2003/0036783 A1 | 2/2003 | Bauhahn et al. |
| 2003/0040700 A1 | 2/2003 | Hickle et al. |
| 2003/0040722 A1 * | 2/2003 | Massengale et al. ......... 604/255 |
| 2003/0050621 A1 | 3/2003 | Lebel et al. |
| 2003/0055406 A1 | 3/2003 | Lebel et al. |
| 2003/0055570 A1 | 3/2003 | Ribeiro, Jr. |
| 2003/0060753 A1 | 3/2003 | Starkweather et al. |
| 2003/0060765 A1 | 3/2003 | Campbell et al. |
| 2003/0065308 A1 | 4/2003 | Lebel et al. |
| 2003/0065370 A1 | 4/2003 | Lebel et al. |
| 2003/0097092 A1 | 5/2003 | Flaherty |
| 2003/0099158 A1 | 5/2003 | De La Huerga |
| 2003/0100864 A1 | 5/2003 | Bendsen et al. |
| 2003/0114836 A1 | 6/2003 | Estes et al. |
| 2003/0135388 A1 * | 7/2003 | Martucci et al. ............... 705/2 |
| 2003/0139701 A1 * | 7/2003 | White et al. ............... 604/67 |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2004/0104271 A1 | 6/2004 | Martucci et al. |
| 2004/0167804 A1 | 8/2004 | Simpson et al. |
| 2004/0176984 A1 | 9/2004 | White et al. |
| 2005/0091338 A1 | 4/2005 | De La Huerga |
| 2005/0144043 A1 | 6/2005 | Holland et al. |
| 2005/0267402 A1 * | 12/2005 | Stewart et al. ............... 604/65 |
| 2005/0277873 A1 * | 12/2005 | Stewart et al. ............... 604/93.01 |
| 2005/0277890 A1 * | 12/2005 | Stewart et al. ............... 604/189 |
| 2005/0277911 A1 * | 12/2005 | Stewart et al. ............... 604/890.1 |
| 2005/0278194 A1 | 12/2005 | Holland et al. |
| 2006/0053036 A1 | 3/2006 | Coffman et al. |
| 2006/0089854 A1 | 4/2006 | Holland et al. |
| 2006/0089855 A1 | 4/2006 | Holland |
| 2006/0106649 A1 | 5/2006 | Eggers et al. |
| 2006/0122867 A1 | 6/2006 | Eggers et al. |
| 2006/0136271 A1 | 6/2006 | Eggers et al. |
| 2006/0143051 A1 | 6/2006 | Eggers et al. |
| 2006/0190302 A1 | 8/2006 | Eggers et al. |
| 2007/0088249 A1 | 4/2007 | Duffy et al. |
| 2007/0204497 A1 | 9/2007 | De La Huerga |
| 2007/0214003 A1 | 9/2007 | Holland et al. |
| 2008/0133265 A1 | 6/2008 | Silkaitis et al. |

FOREIGN PATENT DOCUMENTS

| | | |
|---|---|---|
| JP | 2003/25176 | 1/2003 |
| JP | 2003/70803 | 3/2003 |

OTHER PUBLICATIONS

Response to Final Rejection dated May 14, 2009 to USPTO for U.S. Appl. No. 10/855,872, Aug. 12, 2009.

Letter from Telaric Ideas to Robert W. Connors dated Apr. 29, 2008.

Final Rejection from USPTO for U.S. Appl. No. 10/855,872, Apr. 15, 2010.

* cited by examiner

MEDICAL DEVICE CONFIGURATION BASED ON RECOGNITION OF IDENTIFICATION INFORMATION

CROSS REFERENCE TO APPLICATIONS

This application expressly incorporates by reference, and makes a part hereof, the following U.S. patents and U.S. patent applications: U.S. Pat. No. 5,782,805; U.S. Pat. No. 5,842,841; U.S. patent application Ser. No. 10/855,873; U.S. patent application Ser. No. 10/855,872; and U.S. patent application Ser. No. 10/855,857.

TECHNICAL FIELD

The instant invention relates generally to medical delivery systems and more particularly to administration line sets for use with medical delivery devices and a system for identifying information associated with the line set.

BACKGROUND OF THE INVENTION

The administration of therapeutic fluids to a patient is well known in the art. Many types of medical delivery devices exist to deliver various therapeutic fluids to a patient, such as, for example, parenteral fluids, drugs or other medicaments, electrolytes, blood and blood products, and the like. One particular type of medical delivery device is an infusion pump, which can deliver one or more of these therapeutic fluids to a patient via a variety of administration types, such as, for example, intravenous (IV), intra-arterial (IA), subcutaneous, epidural, irrigation of fluid spaces applications, and the like. Many medical delivery devices that operate under these types of administration typically utilize an administration line set and an associated container containing one or more therapeutic fluids. In the case of an infusion pump, the line set is typically loaded into a delivery mechanism of the pump, which facilitates delivery of the fluid to the patient.

Each type of administration and each type of therapeutic fluid typically involve numerous operational parameters, variables, constraints and other related information, such as medical and pharmaceutical related information, that must be monitored and followed to ensure proper, effective and safe delivery of therapeutic fluids to the patient and effective treatment of the patient. The nature and the amount of this information make its entry into a medical device a daunting task that can be susceptible to human error. Even though most known delivery devices are microprocessor-controlled, software-driven units having associated memory and are thus capable of customization and control by a user—typically via a download of specific data or software from another source—there remains a risk of improperly matching data and software to the appropriate therapy, drug or fluid, or administration set, especially from a logistical standpoint. Additionally, presently known delivery devices, such as infusion pumps, operate within a fixed operating configuration with a fixed set of functionality, regardless of the therapy, drug or fluid, or administration set. This can be another source of error. The potential for error in the delivery of fluids to a patient are numerous and the minimization of such potential is an important goal.

The present invention addresses these and other issues and generally provides new and improved systems, devices and methods associated with administration line sets and associated therapeutic fluids for use with medical delivery devices for delivery of the fluids to a patient.

SUMMARY OF THE INVENTION

The present invention provides a medication delivery system for delivering a medicament or fluid to a patient. According to a particular aspect of the present invention, a disposable element is provided having an identifier. A medical device associated with the system is capable of recognizing the identifier. In particular embodiment, the system comprises a line set associated with a container containing the fluid, an identifier associated with the line set and having identification information associated therewith, and a delivery device configured to engage the line set and deliver the fluid to the patient. The delivery device includes a recognition system that is capable of obtaining the identification information associated with the identifier.

According to another aspect, the identification information is obtained by the device upon engagement between the device and the line set. The identification information may include information regarding the identification of the fluid, a type of line set, or a type of administration associated with the line set.

According to another aspect, the identifier may be a bar code, a passive RF device, a magnetic device, a non-volatile memory device, or the like.

According to another aspect, the identifier may be integrated with a slide clamp associated with the line set.

According to another aspect, the delivery device may include a slide clamp receptacle configured to accept the slide clamp associated with the line set.

According to another aspect, the recognition system can be integrated with the slide clamp receptacle.

According to yet another aspect, the device can be capable of configuration based on the identification information.

According to yet another aspect, the device is automatically configured when the identification information is obtained from the identifier.

According to yet another aspect, the device, upon configuration, is capable of functionality specifically associated with the identification information.

According to another aspect, a disposable element such as a MEMS pump can be utilized in the system of the present invention.

These and other aspects of the present invention will be apparent from the drawings and written specification set forth herein, including the appended claims.

DETAILED DESCRIPTION OF THE PREFERRED EMBODIMENTS

Figure 1:
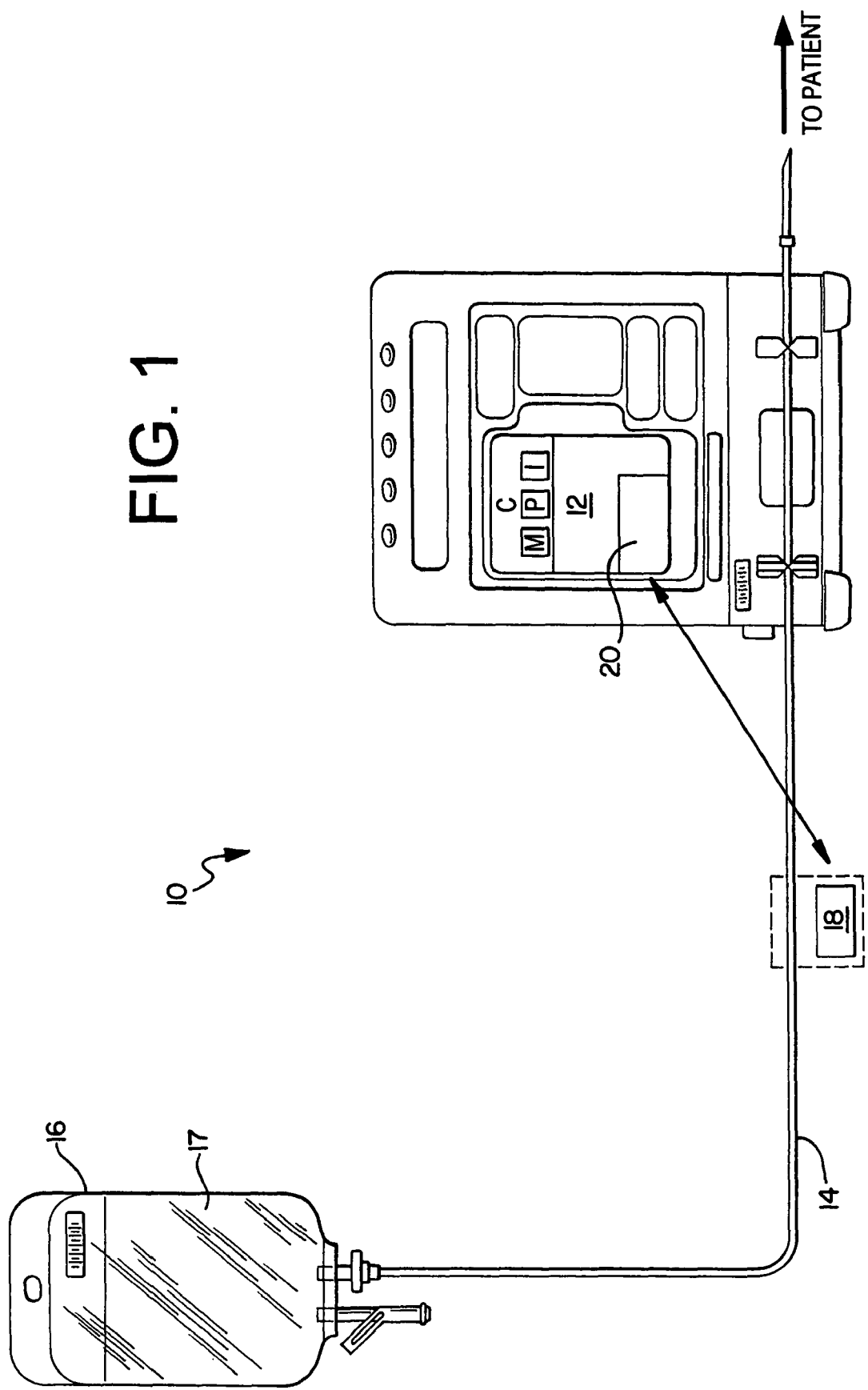
FIG. 1 is a general schematic diagram of a medical delivery system in accordance with the principles of the present invention.

While this invention is susceptible to embodiments in many different forms, there are shown in the drawings and herein described in detail, preferred embodiments of the invention with the understanding that the present disclosures are to be considered as exemplifications of the principles of the invention and are not intended to limit the broad aspects of the invention to the embodiments illustrated.

Referring to FIG. 1, a medication delivery system or medical fluid delivery system 10 is generically depicted. The system 10 includes a medical delivery device 12 including a controller (C) having an associated memory (M), a processor (P) and an input device (I). While the controller (C) is preferably integrated with the device 12, it should be noted that the controller (C) can also be separate and/or distinct from the device 12. For example, the controller (C) may be associated with a personal digital assistant (PDA) or other external computing device, which is distinct from the device 12.

Referring again to FIG. 1, the system 10 further includes at least one administration line set 14, which may be considered a disposable member or disposable element. The line set 14 may be in communication with a container 16 containing medicament 17, or a fluid 17, to be delivered to a patient. The combination of the line set 14 and the container 16 containing the fluid 17 is sometimes referred to as an administration kit. The container 16 can take a variety of different forms, and in one preferred embodiment, the container is a flexible bag. The line set 14 generally includes a tubing having an end connected to or otherwise in communication with the container 16 and another end having a catheter or other device for communication with the patient. The device 12 acts on a portion of the line set 14 to deliver the fluid 17 to the patient. The device 12 may be of any type capable of delivering various fluids to a patient, such as, for example, parenteral fluids, drugs or other medicaments, electrolytes, blood and blood products, and the like. The fluid 17 may comprise any flowable substance that can be delivered to a patient. The device 12 can deliver one or more types of fluids to a patient via a variety of administration types, such as, for example, intravenous (IV), intra-arterial (IA), subcutaneous, epidural, irrigation of fluid spaces applications, and the like. One preferred form of the device 12 is an infusion pump such as the one disclosed in U.S. Pat. Nos. 5,782,805 and 5,842,841, which are hereby incorporated by reference and made a part hereof.

As shown in FIG. 1, an identifier 18 is associated with the administration line set 14. The identifier 18 may further be referred to as an indicia 18. The identifier 18 may be physically attached to, loosely associated with, or in the vicinity of, the line set 14. The identifier 18 may also be integral with the line set 14 or separately attached. The identifier 18 has identification information associated therewith. The identification information, which can comprise an identification code or a data set made up of multiple data components or a single component of data, can be any type of information that the device 12 can utilize in operation and carrying out treatment of a patient. In a preferred embodiment, the identification information includes information regarding identification of the patient, the medicament or fluid 17, a type of the line set 14, a type of administration associated with the line set 14, the material forming the line set 14 (e.g., PVC, non-PVC) and/or other operational parameters. The identification information may also include information regarding the durometer of the line set, dimensions of the line set such as outside and inside diameter data, micro-bore information and/or other parameters necessary to accurately deliver medicament through the line set. With regard to the medicament, the identifier 18 may include identification information such as a drug identification number as is known in the art. The identifier 18 may also contain information concerning: the patient, such as the patient name, age, sex, weight, allergies, disease, condition, etc.; the medicine connected as part of the line set 14 (i.e., in the container 16), such as the drug/non-drug type, name, concentration, etc.; and, the medication therapy to be conducted with the line set 14, including all or any of the process parameters necessary for the medication therapy. Such process parameters may include at least medication type, medication concentration, medication amount, individual bolus volume, total bolus volume, bolus rate, dose, timing between bolus deliveries, maximum number of boluses, maximum number of boluses per unit time, loading dose volume, loading dose rate, loading dose time, maintenance rate, maintenance volume, maintenance time, maintenance dose, diluent volume and patient weight. Finally, the identifier 18 may include information concerning profile data, including but not limited to patient profiles data such as patient pain state, chronologic age, age group, and gestational age, and condition profile data such as the medical condition or medical disease state, including but not limited to renal disease, congenital heart disease, and liver failure. In addition to including specific medication therapy information, the identifier 18 may also include generic medication therapy. For example, the identifier 18 may include process parameters and data applicable to a variety of medications, a category of medications, or to a category of patient and/or condition profiles.

The information or code for the identifier 18 may be provided by a programming device and installed onto the identifier 18. As explained in greater detail below, the identifier 18 may be associated with a medical device wherein the medical device is enacted by recognition of the identifier 18. The identifier 18 may also be programmed with an additional component or identification bit that allows the identification information or data code to be re-used by the programming device in a subsequent system. This will also be described with respect to other embodiments below.

The identifier 18 may be attached to the line set 14 by the manufacturer of the line set 14, by the hospital pharmacy, or by some other entity. When the identifier 18 is attached to the line set 14 by the manufacturer, the line set typically does not yet include a container 16. As such, the line set 14 with the identifier 18 may be pre-made and provided as having information applicable to a category or group of medications. This line set 14, with the identifier 18, may then be attached to a container 16 having medication within this category. Alternatively, the line set 14 may be highly customized and contain many of the patient specific and/or therapy specific process parameters identified above. Such customization is typically performed by a pharmacy wherein a specific prescription and therapy instructions are added to the identification identifier 18.

The identifier 18 can be in any form, such as, for example, a bar code or other IR technology, an RFID, such as an RFID tag, any other passive RF device that can be interrogated, a magnetic storage device, a non-volatile memory, or any other device or technology that can represent information to, and allow retrieval by, another device or system. The device 12 includes a recognition system 20 that is capable of recognizing the identifier 18 and/or obtaining, or retrieving, the identification information for use by the device 12. In a preferred embodiment, the recognition system 20 is part of the controller (C). The form of the recognition system 20 will depend on the particular form of the identifier 18 and associated technology. For example, if the identifier 18 is a bar code, the recognition system will be an IR or other light-emitting device that is capable of reading a bar code. An appropriate form of the recognition system 20 will be apparent to one of skill in the art when the form of the identifier 18 is determined and will include all known devices and technologies that are capable of obtaining or retrieving the identification information from the particular form of the identifier 18. It is understood that the identifier 18 and the recognition system 20 can be used such that once the identifier 18 is in a predetermined vicinity of the recognition system 20 without a physical connection or confronting relation, the recognition system 20 can recognize and identify the information associated with the identifier 18.

Figure 2:
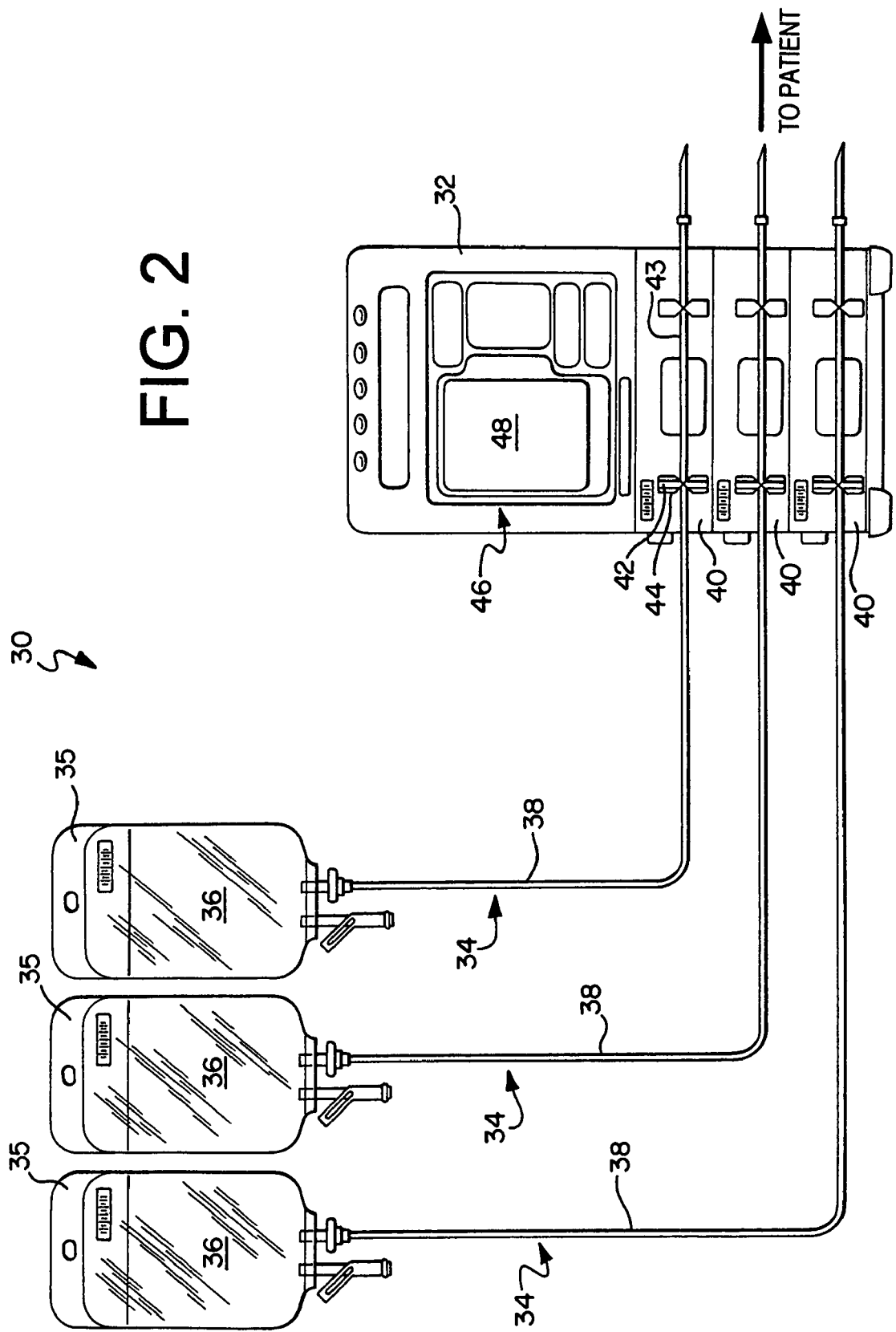
FIG. 2 is a schematic diagram of a particular embodiment of the medical delivery system generally schematically depicted in FIG. 1, including a medical infusion pump.

FIG. 2 depicts a preferred embodiment in the form of a medical delivery system 30. The system 30 includes an infusion pump 32 and at least one administration line set 34 associated with a container 35 containing a fluid 36 to be delivered to a patient. It should be noted that the infusion pump 32 can be of any type of infusion pump, including, for example, volumetric infusion pumps, peristaltic pumps, cassette pumps, syringe pumps or MEMS (micro-electromechanical system) pumps. The infusion pump 32 is preferably a microprocessor-based pump that is capable of being programmed, utilizing software and/or firmware, to facilitate operation and functionality of the pump 32. Software is preferably stored on a computer-readable storage medium resident in the controller (C) of the pump 32, such as, for example, the memory (M). The line set 34 includes a fluid tube 38 that is engaged by the pump 32 and facilitates flow of the fluid 36 to the pump 32. The system 30 is depicted in FIG. 2 as having three administration line sets 34, although a single line set and a single channel pump could be used. The pump 32 can deliver one or more types of fluids to a patient via a variety of administration types, such as, for example, intravenous (IV), intra-arterial (IA), subcutaneous, epidural, irrigation of fluid spaces applications, and the like. Types of fluids may include, for example, parenteral fluids, drugs or other medicaments, electrolytes, blood and blood products, and the like. In this particular embodiment, the pump 32 includes three channels 40, each configured to accept the tube 38 of one of the line sets 34. As is well known in the art, the channels 40 of the pump operate to deliver the fluid 36 from the container 35, through the tube 38 of the line set 34 and to the patient. Each of the administration line sets 34 include a slide clamp 42, such as the one shown in more detail in FIG. 3. The slide clamp 42 is configured to engage the tube 38 of the line set to prevent unwanted flow through the tube until it is loaded into a tube receptacle 43 associated with the pump channel 40. The pump includes a slide clamp receptacle 44 for each of the channels 40.

Figure 3:
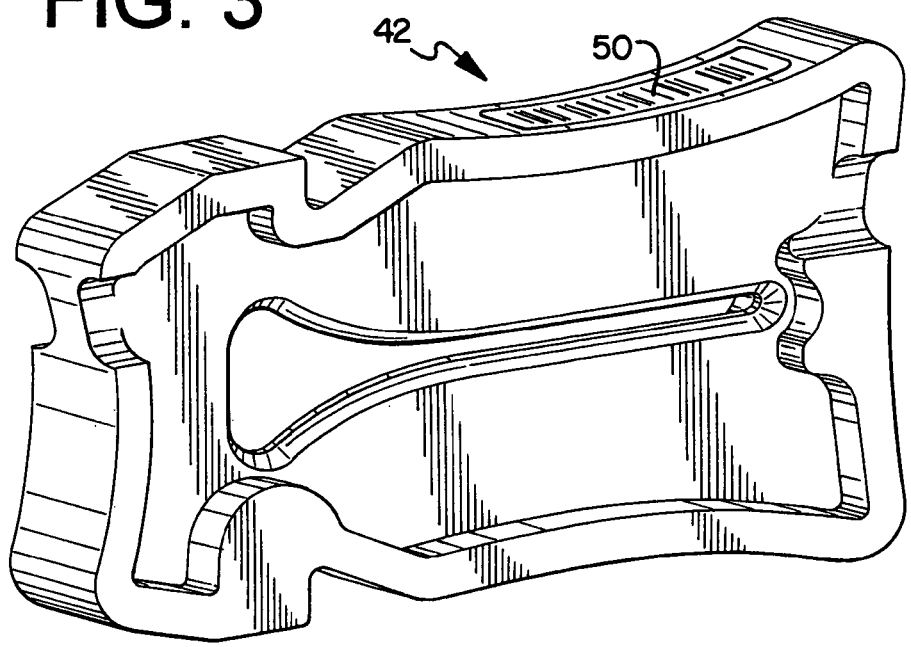
FIG. 3 is a perspective view of a slide clamp for use with an administration line set in accordance with the principles of the present invention.

In one preferred embodiment, the slide clamp 42 includes the identifier 18 as previously described. The slide clamp 42 and identifier 18 may also be considered disposable. The identifier 18 of the slide clamp 42 can be in any form, such as, for example, a bar code (including but not limited to one-dimensional or two-dimensional bar codes) or other IR technology, an RFID, such as an RFID tag, any other passive RF device or transponder that can be interrogated, a magnetic storage device, a non-volatile memory, or any other device or technology that can represent the identification information to, and allow retrieval by, the pump 32. The pump 32 includes the recognition system 20 as previously described that is capable of recognizing the identifier 18 and/or obtaining, or retrieving, the identification information for use by the pump 32. In a preferred embodiment, the identifier 18 is a bar code 50 on the slide clamp 42, as shown in FIG. 3, and the recognition system 20 is a bar code reader (in a preferred embodiment, is integrated into the clamp receptacle 44) that can interrogate the bar code 50 and obtain the identification information for use by the pump 32. In a preferred embodiment, the identification information includes information regarding identification of the medicament 36, or fluid 36, a type of the line set 34, a type of administration associated with the line set 34, and/or other desired information, such as, for example, an age of a patient or other patient data, a type of therapy, a type of disease, and a type of condition of the patient. It is further understood that the identifier 18 can be located on a number of different locations of the slide clamp 42. The recognition system 20 is positioned accordingly based on the position of the identifier 18 or the slide clamp 42.

When the pump 32 obtains the identification information from the identifier 18, the pump 32 can utilize this information in a number of ways, including to alter operation of the pump. For example, once the pump 32 obtains the identification information, the pump 32 can be configured in accordance with the identification information. In a preferred embodiment, the pump 32 is automatically configured when the identification information is obtained from the identifier 18, or configured in response to obtaining the information. Configuration may include set up and/or execution of any number of operational parameters and/or user interfaces of the pump 32. For example, upon configuration, the pump operating system may modify availability of certain functionality, such as by adding or enabling certain functionality specifically associated with the identification information. For example, configuration may include enabling a function that should only be available for a particular type of administration, fluid or line set. Conversely, the pump operating system may modify availability of certain functionality by disabling functionality for particular types of administrations, fluids or line sets. For example, the identifier 18 may include information that identifies the type of line set 34 being used, e.g., epidural. Based on identification of the line set 34 being an epidural line set, subsequent operation of the pump 32 and treatment of the patient can be dictated by this initial identification. The pump 32 could also be configured to operate based on recognition of a type of material that forms the line set 34.

The configuration aspect of the present invention can have numerous applications within the context of a medical delivery system. While some examples of specific configurations are described herein, it should be understood that there are numerous other potential configurations that are achievable, alone or in combination, in accordance with the basic principles of the present invention, and although not specifically described, are nevertheless intended to be within the scope of the present invention by virtue of their application of these principles.

In accordance with the principles of the present invention, the controller (C) of the pump 32 can be configured to facilitate configuration of the pump based on a set of configuration information associated with predetermined identification information, which is preloaded in the memory (M). In such cases, the recognition system receives identification information from the identifier associated with the administration line set and the processor retrieves the set of configuration information associated with the received identification information based on a comparison of the predetermined identification information with the received identification information. Upon a match between the received identification information and the predetermined identification information, the processor configures the controller based on the set of configuration information. Match criteria can be defined in a number of ways, such as, for example, a match between a type of line set or type of administration associated with a line set. The match criteria may also be defined by identification of certain parameters or values associated with the identification information, such as, for example, identification of a parameter or value falling within a predetermined range. It is contemplated that a healthcare facility can customize the controller of the pump by defining the predetermined identification information, match criteria and/or the preloaded set of configuration information or profiles.

In certain instances, it may be desirable to modify availability of features and functions of the pump 32 based on the identification information, such as add functionality to, or enabling functionality on the pump 32 for certain identification information or other criteria. For example, the added functionality may include messaging specifically associated with the identification information, such as messaging to a user regarding unique characteristics of a particular type of fluid or administration line set. The added functionality may also include accessibility by a user to a set of guidelines for administration of a particular fluid, such as guidelines for the recommended administration of a particular drug. The added functionality may also include accessibility by a user to a set of guidelines on a predetermined policy, such as a policy set by a hospital, regarding line set changes. The functionality may include certain notifications, such as notification to a user of a type of administration associated with a particular fluid. In certain instances, it may be desirable to provide functionality that includes linking a user to certain types of information, such as a drug protocol associated with a drug identified by the identification information. In this example, the protocol may include information regarding dosing and administration specific to the drug. In other instances, it may be desirable to add functionality that includes a warning system, which may include an alarm, for drug incompatibility based on identification of a particular drug. In some instances, it may also be desirable to add functionality that includes an escalating alarm function, which provides for escalation of an alarm associated with a particular event associated with treatment when the alarm is not addressed by a caregiver. In certain instances, it may also be desirable to remove from, or disable functionality on the pump 32 based on the identification information. For example, a particular function may be disabled based on the identification information, such as disablement of a function based on an identification of a type of administration. As a more specific example, the function of automatic piggybacking may be disabled on the pump 32 based on identification of an epidural type of administration.

The configuration may include adjustments or changes to the system. For example, an adjustment to a sensing system of the pump 32 may be desirable based on the identification information.

It is also contemplated that the configuration may include functionality based on identification of a treatment system, such as identification of a specific combination of container, fluid, line set, and/or administration type, e.g., an administration line set kit. In such instances, functionality may be added that is treatment system specific, such as the addition of notifications or guidelines for the specific combination. For example, a particular fluid container and line set combination, such as a combination included in a particular line set kit, may have certain guidelines applicable only to the particular combination.

Figure 4:
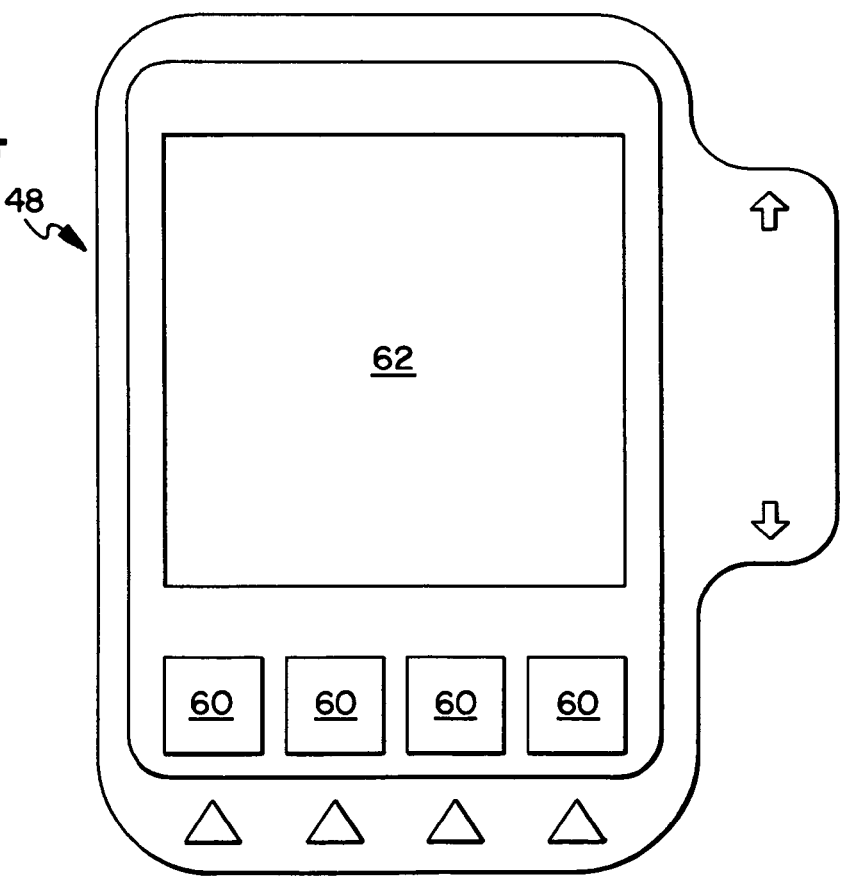
FIG. 4 is a generic screen shot of a display of the medical pump depicted in FIG. 2, showing various fields of the display that can be configured in accordance with identification information obtained by the pump.

The configuration may also include changes to a user interface 46 (shown in FIG. 2) of the pump 32 based on the configuration. For example, as shown in FIG. 4, added functionality may require the addition of one or more soft-keys 60 on a display 48 of the pump 32. Certain labels, messaging or other information may also be provided on the display 48 within a display field 62 of the display 48 based on the added functionality. Conversely, certain soft-keys 60 may be "grayed-out" or removed if certain functionality is disabled and certain labels or information within the display field 62 may be removed. The display field 62 can be further divided into smaller sub-fields that can also be customized. It should be noted that the soft-keys 60 can alternatively serve as labels for hard keys (not shown) on the user interface 46 of the pump 32. It should be apparent that when the user interface of the pump 32 is customized based on the identification information, many sources of potential error can be eliminated.

The identification information associated with the identifier 18 can also be used in diagnostic applications. For example, the information may indicate to the pump 32 that certain tests or diagnostic routines should be performed. It is also contemplated that the identifier 18 can be associated with a diagnostic line set. In this case, specific operational parameters, mechanisms, and alarms on the pump 32 can be evaluated for proper operation when the diagnostic line set is loaded into the pump 32 and the pump 32 recognizes the identification information as indicating that a diagnostic line set has been loaded. For example, the identifier 18 associated with a diagnostic line set can instruct the pump 32 to perform a check and certify that associated alarms are in proper working order. A diagnostic administration kit may include a container containing a particular fluid to be used in the testing. In such case, once the pump 32 recognizes the identifier 18 associated with the diagnostic kit, the pump 32 can run a series of checks wherein the expected operational parameters of the pump 32 based on the particular fluid can be used as a diagnostic benchmark.

Figure 5:
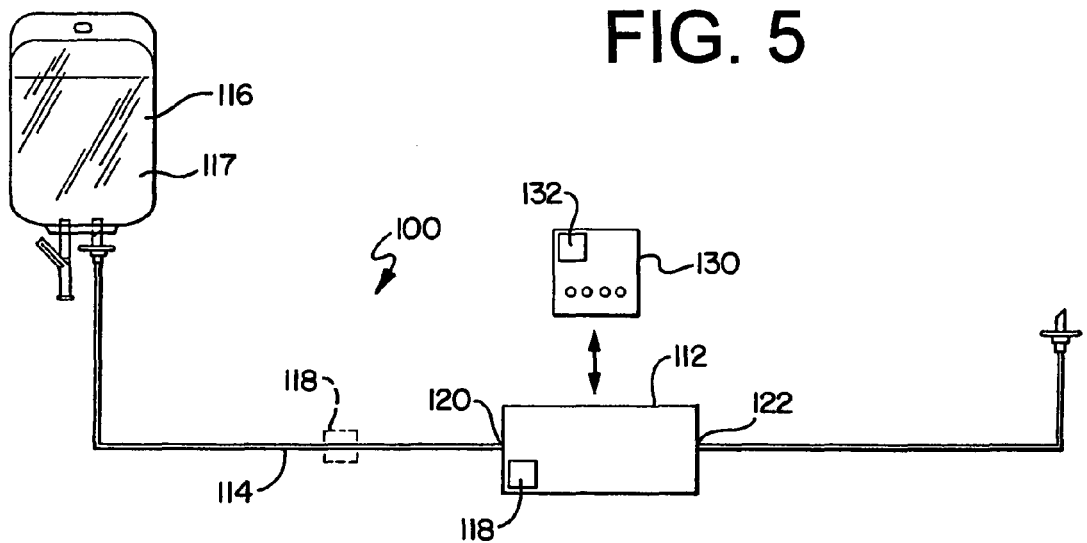
FIG. 5 is a schematic diagram of a medical delivery system according to another embodiment of the present invention.

FIG. 5 shows another embodiment of a system of the present invention, generally designated with the reference numeral 100. Similar to the embodiments described above, the system 100 utilizes a disposable element and an identifier. In one preferred embodiment, a disposable element such as a disposable pump is utilized. The disposable pump can be a micro-pump or a MEMS (micro electromechanical system) pump, or other type of disposable pump. As shown in FIG. 5, the system 100 generally includes a medical device 112, preferably a MEMS pump, an administration line set 114 and a container 116. The system 100 may also take the form of any of the systems such as disclosed in commonly-owned U.S. patent application Ser. No. 10/040,887, entitled "Infusion System," which application is expressly incorporated by reference herein.

The container 116 is a container similar to the container 16 described above. In one preferred embodiment, the container 116 is a flexible bag adapted to contain a medication, or medicament, such as a medical fluid. The administration line set 114 is similar the line set 14 described above. The line set 114 includes a tubing having one end connected to or otherwise in communication with the container 116 and another end having a catheter or other device for communication with the patient.

As further shown in FIG. 5, the MEMS pump 112 is operably associated with the line set 114. The MEMS pump 112 may be connected to the line set 114 in various configurations. For example, the MEMS pump 112 may have an inlet port 120 and an outlet port 122 wherein the MEMS pump 112 is connected at an intermediate portion of the line set 114. Accordingly, a portion of the line set 114 is connected to the inlet port 120 and a portion of the line set 114 is connected to the outlet port 122 wherein the MEMS pump 112 is operably connected to the line set 114. Once properly connected, the MEMS pump 112 can pump fluid from the container 116, through the line set 114 and to the patient. The disposable pump 112 could further be incorporated into an interior of the line set 114 or otherwise take some integral form with the line set 114.

As discussed, the pump 112 may be a MEMS pump 112. MEMS devices are typically etched in silicon. It is further understood that MEMS may also describe other types of micro electromechanical system devices such as devices that are micro-molded in plastic. Thus, MEMS devices may include devices etched in silicon, molded in plastic or otherwise fabricated on a small scale.

The system 100 may also use an identifier 118. In one preferred embodiment, the identifier 118 is associated with or otherwise connected to the MEMS pump 112. It is understood, however, that the identifier 118 may also be associated with other elements, and connected at other locations such as the disposable line set 114 as shown in FIG. 5. The identifier 118 is similar as described above and can contain any of the information or identifying indicia or data as described above.

The system 100 may further use a controller 130. The controller 130 is operably associated with the MEMS pump 112. The controller 130 may communicate with the MEMS pump 112 via a wireless connection. Alternatively, a hard connection may be utilized wherein the MEMS pump 112 may be plugged into the controller 130. It is further understood that the controller 130 can be integral as part of the MEMS pump 112. It is further understood that the controller 130 can be a separate hand-held computer or a separate network controller that controls the pump 112 via a network communication link. Similar to the discussion above, the controller 130 has a recognition system 132. The recognition system 132 is capable of recognizing the data contained in the identifier 118.

The recognition system 132 can cooperate with the identifier 118 to operate the system 100. For example, the identifier 118 may contain information that identifies the type of line set 114 connected to the MEMS pump 112. The identifier 118 may further container any of the other types of information as described above. The information contained on the identifier 118 may also include data relating to functionality that instructs the controller 130 in controlling operation of the MEMS pump 112. It is further understood that the disposable element such as the MEMS pump 112 can be activated by a separate patient care system.

It is understood that the disposable element can take a variety of different forms. The disposable element could be considered the MEMS pump 112 or the line set 114, or the combination of both elements. In addition, other types of MEMS components could also be used in the system 100.

Figure 6:
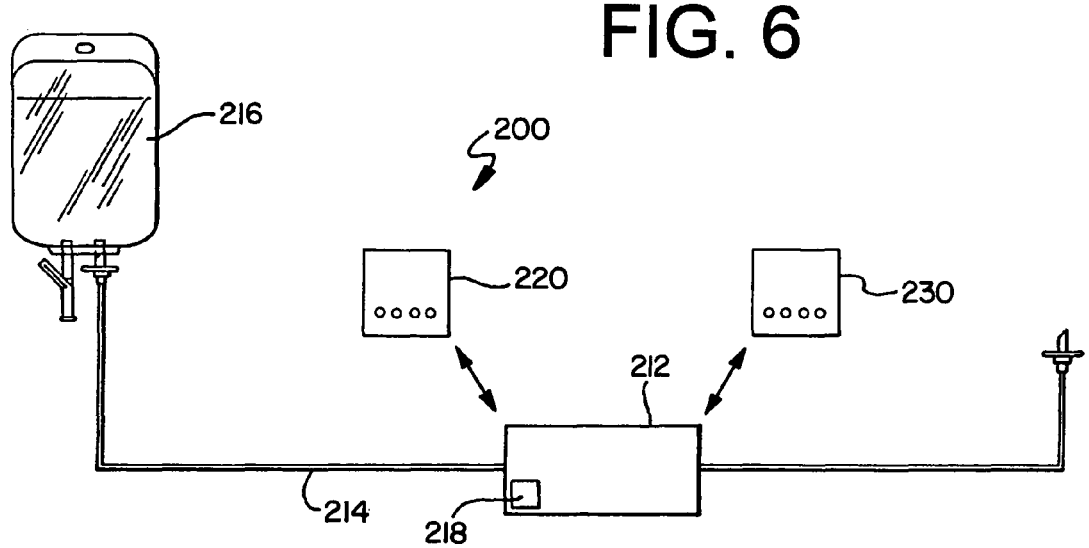
FIG. 6 is a schematic diagram of a medical delivery system according to another embodiment of the present invention.

FIG. 6 discloses another embodiment of a system of the present invention, generally designated with the reference numeral 200. Similar to the embodiments described above, the system 200 utilizes a disposable element and an identifier. Similar to the system 100 of FIG. 5, a MEMS component such as a MEMS pump is utilized. As shown in FIG. 6, the system 200 generally includes a medical device 212, preferably a MEMS pump 212, an administration line set 214 and a container 216. The system further includes a programming device 220 and a controller 230.

Similar to the systems described above, an identifier 218 is associated with a disposable element. In the preferred embodiment of FIG. 6, the identifier 218 is associated with the MEMS pump 212 and can contain any of the data as previously described. As further shown in FIG. 6, a programming device 220 is utilized to program the identifier 218 with the desired data, identification code or other identifying information. As part of this programming function, the programming device 220 may program the identifier 218 with an additional identification component to be used at a separate stage of the system 200. It is understood that the identifier 218 will be a device having memory as is known and also be capable of being re-configurable, re-settable or changeable. Once programmed by the programming device 220, the MEMS pump 212 may be activated by a controller 230. The controller 230 may be part of an overall patient care system operated, for example, in a hospital setting. In one embodiment, the controller 230 could be in the form of a hand-held computer such as a personal digital assistant. The controller 230 recognizes the identifier 218 and activates the pump 212. Once activated, the controller 230 controls the MEMS pump 212 wherein the pump 212 operates to deliver medication to a patient. The pump 212 has the ability to recognize a predetermined event such as when the fluid is generally substantially pumped from the container 216 to define a generally empty container. For example, a predetermined pressure sensed by the MEMS pump 212, once reached, could cause the MEMS pump 212 to shut down. Once the MEMS pump 212 shuts down, this condition could trigger the additional identification component, stored in memory with the identifier 218, or at another location in a separate memory device, to change the state of the additional identification component to indicate that the MEMS pump 212 has shut down. Thus, when the pump 212 recognizes that the container 216 is empty, the additional identification component changes state in memory and may be considered to be activated. Upon activation, the additional identification component is capable of being recognized. This recognition can take various forms. For example, in one embodiment, a signal is communicated back to the controller 230 and/or the programming device 220 to indicate to the programming device 220 that the original identification data may be re-used in a subsequent operation of a system 200. Alternatively, the controller 230 and/or programming device 220 can pull or read the additional information component from its location such as on the identifier 218 on the pump 212. Thus, the additional identification component allows for the identifier 218 to comprise a reusable identification component. In addition, the identifier 218 is capable of being settable and then re-settable or configurable and then re-configurable (e.g. changeable). In one embodiment, the identifier 218 is an RFID identifier. The component can also comprise any form of electrically-alterable non-volatile memory. It is understood that the communication can be directly to the programming device 220 or communicated through the controller 230. By using the additional identification component, or additional information bit, the identification code can be re-used to enhance overall operation of the system. Also, it is understood that the predetermined event described above could also be an event such as when the controller indicates an end to an infusion therapy (e.g., independent of the amount of medicament remaining in the container).

It is further understood that while the additional identification component can be re-used for a new infusion therapy with a new set of system components, the system is configured such that it will not allow the additional identification component to be used with the same components as in the original therapy. Thus, the additional identification component and for example, the disposable MEMS pump used in a first infusion therapy cannot be re-used together in a second infusion therapy. If this was attempted, the system would not operate for the second infusion therapy. The additional identification component can only be used with new components for a new therapy.

Additional features can be utilized with any of the embodiments described above. As discussed, a kit can be formed that may include the container 16, the line set 14 and the identifier 18. The identifier 18 can be associated with or connected to either of the container 16 and the line set 14. In some embodiments, the container 16 may contain a pre-attached reconstitution device having a pre-attached drug container such as a vial. The reconstitution device could be activated to reconstitute the drug with the fluid 17 in the container 16. It is understood that the identifier 18 can also include information regarding the vial that may be pre-attached to the reconstitution device. In another embodiment, a disposable pump such as a micro-pump or MEMS pump can also be connected to the line set 14 and be considered as part of the kit. The identifier 18 associated with such kits can have any of the information described above for overall proper operation of the system. In yet another embodiment, the container 16, or container 16 associated with the kit may include a pre-mixed medicament 17. The identifier 18 associated with the pre-mixed medicament 17 can have an expiration date associated therewith. The delivery device or pump used with such kit has the recognition system that recognizes the identifier 18 and a date of operation of the pump. The pump is configured such that it will not operate if the recognition system determines the operation date is a date after the recognized expiration date. Thus, if the recognition system of the pump reads an expired date, the pump will not operate and give an indication of an expired medicament. In one preferred embodiment, the system will also include an alarm system operably associated with the system that is capable of generating an alarm if an expired medicament is detected. The alarm can take many different forms and may have audible components, visual components or a combination of both.

It is further understood that a pump utilized in the present invention will incorporate safety software. The safety software is capable of generating basic failure alarms wherein the pump would assume a fail safe condition such as no free flow of medicament through the pump. Various software/pump configurations may be utilized. For example, all software may be located on the pump head, or all software may be located off of, or remote from the pump head. In addition, all software may be located off of the pump head with the exception of the specific safety software being located on the pump head.

SPECIFIC EXAMPLES

Two specific examples of the application of the principles of the present invention will now be described.

In the first example, an administration line set having an identifier is loaded into the pump. Upon insertion of the slide clamp into the slide clamp receptacle on the pump, the recognition system of the pump obtains the identification information from the identifier. In this example, the identification information indicates to the pump that the type of administration associated with the line set that was loaded into the pump is enteral. Based on the identification of the enteral administration type, the pump software performs a configuration of the pump for enteral administration based on one of a set of administration line set profiles associated with enteral administration. In this particular example, the recordation of volume history is enabled by the pump.

In the second example, an administration line set having an identifier is loaded into the pump. Upon insertion of the slide clamp into the slide clamp receptacle on the pump, the recognition system of the pump obtains the identification information from the identifier. In this example, the identification information indicates to the pump that the type of administration associated with the line set that was loaded into the pump is epidural. Based on the identification of the epidural administration type, the pump software performs a configuration of the pump for epidural administration. In this case, the pump enables functionality that includes a continuous drip of the fluid, disablement of a piggy back feature of the pump, disablement of an air line sensor of the pump, and disablement of an occlusion detection feature of the pump.

It should be understood that the invention may be embodied in other specific forms without departing from the spirit or central characteristics thereof. The present embodiments, therefore, are to be considered in all respects illustrative and not restrictive, and the invention is not to be limited to the details given herein.

What is claimed is:

1. A medical delivery system for delivering a medicament to a patient, the system comprising:
    a line set including a line adapted to be connected to a container containing the medicament;
    an identifier integrated with a slide clamp associated with the line set and having identification information including at least one of: (a) a type of line set, (b) a type of administration associated with the line set, (c) a material forming the line set, (d) a durometer of the line set, and (e) at least one dimension of the line set, the slide clamp configured to receive the line in a first direction that is at least substantially coincident with the central axis of the line, the identifier disposed on the slide clamp so as to face a second direction that is at least substantially perpendicular to the first direction, wherein the identifier is one of a bar code, a passive radio frequency ("RF") device, a magnetic device and a non-volatile memory device; and
    a delivery device configured to engage the line set and deliver the medicament to the patient, the delivery device including a slide clamp receptacle configured to accept the slide clamp and including a recognition system, the recognition system of the slide clamp receptacle capable of reading the identification information associated with the identifier, the delivery device capable of configuration based on the identification information.

2. The system of claim 1, wherein the delivery device is automatically configured when the identification information is obtained from the identifier.

3. The system of claim 1, wherein, upon configuration, the delivery device is capable of functionality specifically associated with the identification information.

4. The system of claim 3, wherein the delivery device provides a message specifically associated with the identification information.

5. The system of claim 1, wherein the identification information includes information regarding identification of the medicament.

6. The system of claim 3, wherein the delivery device includes accessibility by a user to a set of guidelines for administration of the fluid.

7. The system of claim 3, wherein the delivery device includes accessibility by a user to a set of guidelines on a predetermined policy regarding line set changes.

8. The system of claim 1, wherein the delivery device includes notification to a user of a type of administration associated with the medicament.

9. The system of claim 1, wherein the delivery device includes disablement of a particular function based on the identification information.

10. The system of claim 9, wherein the particular function that is disabled is automatic piggybacking.

11. The system of claim 3, wherein the delivery device includes disablement of a particular function based on an identification of a type of administration.

12. The system of claim 1, wherein the delivery device includes linking a user to a drug protocol associated with a drug, the protocol including information regarding dosing and administration specific to the drug.

13. The system of claim 1, wherein, upon configuration, an adjustment is made by the device to a sensing system of the device.

14. The system of claim 1, wherein the delivery device includes at least one specific feature related to a system defined by identification of a particular fluid container and line set.

15. The system of claim 1, wherein, upon configuration, at least one operational characteristic of the delivery device is changed.

16. The system of claim 1, wherein the delivery device is an infusion pump.

17. The system of claim 1, wherein the medicament is one of a parenteral fluid, a drug, an electrolyte, blood and a blood product.

18. The system of claim 5, wherein the type of administration is one of intravenous (IV), intra-arterial (IA), subcutaneous, epidural, and irrigation of fluid spaces.

19. The system of claim 1, wherein the delivery device includes a slide clamp receptacle configured to accept the slide clamp associated with the line set.

20. The system of claim 19, wherein the recognition system is integrated with the slide clamp receptacle.

21. The system of claim 1, wherein the identification information includes identification of the type of administration associated with the line set, and, upon configuration, the device is capable of functionality specifically associated with the type of administration.

22. The system of claim 21, wherein the type of administration is enteral.

23. The system of claim 3, wherein the delivery device includes providing for recordation of a volume history.

24. The system of claim 21, wherein the type of administration is epidural.

25. The system of claim 3, wherein the delivery device includes providing for a continuous drip of the fluid.

26. The system of claim 3, wherein the delivery device includes disablement of an air line sensor of the device.

27. The system of claim 3, wherein the delivery device includes disablement of an occlusion detection feature of the device.

* * * * *